US 6,579,906 B2

(12) United States Patent
Cooper et al.

(10) Patent No.: US 6,579,906 B2
(45) Date of Patent: Jun. 17, 2003

(54) DENDRIMER BIOCIDE-SILVER NANOCOMPOSITES: THEIR PREPARATION AND APPLICATIONS AS POTENT ANTIMICROBIALS

(75) Inventors: Stuart L. Cooper, Chicago, IL (US); Chris Z. Chen, Trooper, PA (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/877,931

(22) Filed: Jun. 8, 2001

(65) Prior Publication Data

US 2002/0022012 A1 Feb. 21, 2002

Related U.S. Application Data

(60) Provisional application No. 60/210,888, filed on Jun. 9, 2000.

(51) Int. Cl.⁷ .................. A01N 33/02; A61K 31/74
(52) U.S. Cl. ...................... 514/646; 424/78.17
(58) Field of Search ............... 514/646; 424/78.17

(56) References Cited

U.S. PATENT DOCUMENTS 5,962,423 A    10/1999  Bundle et al. ............ 514/25
6,224,898 B1 *  5/2001  Balogh et al.
6,440,405 B1 *  8/2002  Cooper et al.

FOREIGN PATENT DOCUMENTS

WO    WO 98/06691    2/1998
WO    WO 98/26662    6/1998

OTHER PUBLICATIONS

Chen et al., Book of Abstracts, 218th ACS National Meeting, Aug. 1999, PMSE–118.*
Tomalia (1994), Starburst/Cascade Dendrimers: Fundamental Building Blocks for a New Nanoscopic Chemistry Set, Advanced Materials, vol. 6, No. 7/8, pp. 529–539.
Matthews, Shipway, and Stoddart (1998), Dendrimers—Branching Out From Curiosities Into New Technologies, Prog. Polym. Sci., vol. 23, pp. 1–56.
Tang, Redemann, and Szoka (1996), In Vitro Gene Delivery by Degraded Polyamidoamine Dendrimers, Bioconjugate Chem., vol. 7, pp. 703–714.
Hawker and Wooley (1995), The Convergent–Growth Approach to Dendritic Macromolecules, Department of Chemistry, University of South Florida, vol. 2, pp. 1–39, 41–71, 123–156, and 157–190.
Liu and Uhrich, Hyperbranched Polymeric Micelles: Drug Encapsulation, Release and Polymer Degradation, Department of Chemistry, Rutgers University, pp. 582–583.
Liu and Fréchet, Preparation of Water–soluble Dendritic Unimolecular Micelles as Potential Drug Delivery Agents, Department of Chemistry, University of California, pp. 167–168.

(List continued on next page.)

Primary Examiner—Russell Travers
Assistant Examiner—San-ming Hui
(74) Attorney, Agent, or Firm—Connolly Bove Lodge & Hutz LLP

(57) ABSTRACT

A novel cationic dendrimer biocide-silver nanocomposite and methods for its use as a biocide. The biocidal nanocomposites of the present invention are effective against a variety of microbial species, including anthrax. The invention is also highly stable and safe for exposure to human skin. The invention has applications as an antibiological warfare agents, antimicrobial agent for surface coatings and as a general biocide that is safe for human exposure.

1 Claim, 1 Drawing Sheet

OTHER PUBLICATIONS

Figure 1:
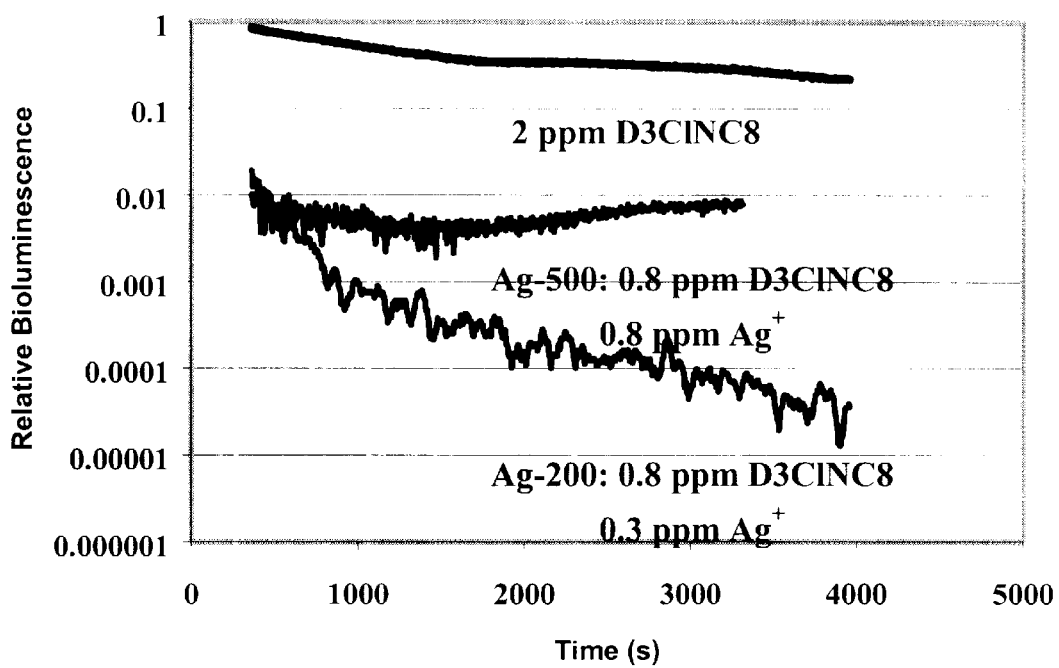

Kukowska–Latallo, Bielinska, Johnson, Spindler, Tamalia and Baker (1996) Efficient transfer of genetic material into mammalian cells using Starburst polyamidoamine dendrimers, Proc. Natl. Acad. Sci., vol. 93, pp. 4897–4902.

Uhrich (1997) Hyperbranched Polymers for Drug Delivery, Department of Chemistry, Wright–Rieman Laboratories, Rutgers University, vol. 5, No. 12, pp. 388–393.

Zeng and Zimmerman (1997) Dendrimers in Supramolecular Chemistry: From Molecular Recognition to Self–Assembly Chem. Rev., American Chemical Society, vol. 97, pp. 1681–1712.

Newkome, He and Moorefield (1999) Suprasupermolecules with Novel Properties: Metallodendrimers, Chem. Rev. American Chemical Society, vol. 99, pp. 1689–1746.

Tomalia, Berry, Hall and Hedstrand (1987) Starburst Dendrimers. 4. Covalently Fixed Unimolecular Assemblages Reminiscent of Spheroidal Micelles, Macromolecules, vol. 20, pp. 1164–1167.

Balough, Laverdure, Gido, Mott, Miller, Ketchel and Tomalia (1999) Dendrimer–metal nanocomposites, Material Research Society Symposium—Proceedings, vol. 576, Proceedings of the 1999 MRS Spring Meeting, Organic/Inorganic Hybrid Nat'l, Apr. 5–9m 1999, San Francisco CA, pp. 69–75.

O. Rahn and W. Eseltine, *Annual Review of Microbiology*, 1, 173–92 (1947).

H. Sommer, L. Jackson, *J. Org. Chem*, 35, 1558 (1970).

H. Sommer, H. Lipp, L. Jackson, *J. Org. Chem*, 36, 824 (1971).

L. Donaruma, O. Vogl, "Polymeric Drugs", p 169–171, 161–182, Academic Press: New York (1978).

"Disinfection, Sterilization, and Preservation", pp. 309–325, 3 ed., Lea and Febiger (1983).

"Anionic Polymeric Drugs", pp. 2–18, John Wiley & Sons: New York

H. Yuan and S. Tazuke, *Polymer Journal*, 15, 125–133 (1983).

D. Tomalia, V. Berry, M. Hall, and D.M. Hedstrand, *Macromolecules*, 20, 1164–1167 (1987).

D. Tomalia, A. Naylor, and W. Goggard, *Agnew. Chem. Int. Ed. Engl.*, 29, 138–175 (1990).

C. Hawker and J.M.J. Frechet, *J. Am. Chem. Soc.*, 112, 7638–7646 (1990).

S. Denyer and Q. Hugo, "Mechanisms of Action of Chemical Biocides", pp. 331–334, Blackwell Scientific Publications: Oxford (1991).

M. Vaara, *Micobiol. Rev.*, 56, 395–411 (1992).

A. Kanazawa, T. Ikeda, and T. Endo, *Journal of Polymer Science*, 31, 335–343 (1993).

A. Kanazawa, T. Ikeda, and T. Endo, *Journal of Polymer Science*, 31, 1441–1447 (1993).

A. Kanazawa, T. Ikeda, and T. Endo, *Journal of Polymer Science*, 31, 1467–1472 (1993).

A. Kanazawa, T. Ikeda, and T. Endo, *Journal of Polymer Science*, 31, 3003–3011 (1993).

A. Kanazawa, T. Ikeda, and T. Endo, *Journal of Polymer Science*, 31, 3031–3038 (1993).

E. M.M. de Bradander–van den Berg and E.W. Meijer, *Agnew. Chem. Int. Ed. Engl.*, 32, 1308–1311 (1993).

J. Frechet, *Science*, 263, 1710–1714 (1994).

R. Roy, *Polymer News*, 21, 226–232 (1996).

G.R. Mewkome, C.N. Moorefield, F. Vogtle, "Dendritic Molecules Concepts Syntheses Perspectives", pp. 2–13, VCH: Weinheim, (1996).

D. Zanini and R. Roy, *J. Am. Chem. Soc.*, 119, 2088–2095 (1997).

H. Hansen, S. Haataja, J. Finne, and G. Magnusson, *J. Am. Chem. Soc.*, 119, 6974–6979 (1997).

M. Mammen. S. Choi, and G. Whitesides, *Agnew. Chem. Int. Ed. Engl.*, 37, 2754–2794 (1998).

Z. Chen, J. Oh, P. Dhurjati, T. Van Dyk, R. LaRossa, and S. Cooper, 24th Annual Meeting of the Society for Biomaterials, Apr. 22–26 San Diego, CA, (1998).

Z. Chen, N. Tan, and S. Cooper, *Chem Commun.*, 1585–1586 (1999).

H. Arimoto, K. Nishmura, T. Kinumi, I. Hayakawa, and D. Uemura, *Chem Commun.*, (1999).

G. Newkome, E. He, and C. Moorefield, Chem. Rev., 99, 1689–1746 (1999).

L. Balogh, A. McManus, D. Tomalia, G. Hagnauer, American Chemical Society Division of Colloid and Surface Chemistry Abstracts, 218th ACS National Meeting, New Orleans, LA, Aug. 22–26 (1999).

* cited by examiner dendrimer biocide-silver nanocomposites: their preparation and applications as potent antimicrobials

CLAIM OF PRIORITY

Priority is claimed under 35 U.S.C. §119(e) from the U.S. Provisional Application Ser. No. 60/210,888 filed Jun. 9, 2000; which is herein incorporated by reference.

BACKGROUND OF THE INVENTION

1. Field of the Invention

The present invention relates to the synthesis and characterization of a series of new compositions of matter, formulations, and applications of dendrimer biocide-silver nanocomposites as potent antimicrobial agents.

2. Description of the Related Art

Dendrimers are well defined, highly branched macromolecules that emanate from a central core. Commercially available dendrimers include polyamidoamine ("PAMAM") dendrimers and polypropylene imine ("PPI") dendrimers. Dendriditic architecture brings a very high number of functional groups in a compact space. Dendrimers in the present invention can for example be selected from the group consisting of polyamidoamine dendrimers, polylysine based dendrimers, polyethylene oxide based dendrimers, silicon based dendrimers, polyether based dendrimer and polypropylene imine dendrimers. A polylysine based dendrimers refers to a dendrimer in which the backbone or structure consists essentially of polylysine. A polyethylene oxide based dendrimers refers to a dendrimer in which the backbone or structure consists essentially of polyethylene oxide. A silicon based dendrimers refers to a dendrimer in which the backbone or structure consists essentially of silicon. A polyether based dendrimer refers to a dendrimer in which the backbone or structure consists essentially of polyether.

The advent of dendrimers represents a major breakthrough in synthetic chemistry. Dendrimers can be tailored to generate uniform or discrete functionalities and possess tunable inner cavities, surface moieties, sizes, molecular weights, and solvent interactions. Dendrimers can be synthesized by a convergent approach, see Tomalia, et al., *Macromolecules*, 20 at 1164 (1987), alternatively, dendrimers can also be synthesized by a divergent approach, see Tang, et al., *Bioconjugate Chem.*, 7 at 703–714 (1996).

In the divergent approach, growth of dendrimers starts from a multi-functional core. Through a series of reaction and purification steps, dendrimers grow radially outwards. At different stages of the synthesis, dendrimers are identified by generations. As the generation increases, the number of functional groups, the size of the dendrimer, and the molecular weight of the dendrimer increase. Commercially available dendrimers, such as polyamidoamine (PAMAM) dendrimers from Dendritech Inc. (Midland, Mich., USA) and polypropylene imine (PPI) dendrimers from DSM (Geleen, Netherlands) are synthesized by the divergent approach.

In the convergent approach, dendrons, as parts of dendrimers, are synthesized according to the divergent approach and these dendrons are then coupled to a multi-functional core. The advantage of the convergent approach is that the chemistry of each dendron can be different, and distinct functional groups can be integrated into dendrimers at precise sites. Due to the repetitive nature of the dendrimer synthesis and the extensive purification required, dendrimers are very expensive and not readily available. The combination of discrete numbers of functionalities in one molecule and high local densities of active groups has attracted a lot of attention, especially for biological applications. The unique architecture of dendrimers, they have been investigated for a wide variety of applications, such as gene delivery vesicles, Tang, et al., *Bioconjugate Chem.*, 7 at 703–714 (1996); Kukowska-Latallo, et al., *Proc. Natl. Acad. Sci. USA*, 93 at 4897–4902 (1996), catalysts, Zeng, F. Z., *S. C. Chem. Rev.*, 97 at 1681 (1997); Newkome, et al., *Chem. Rev.*, 99 at 1689–1746 (1999), drug delivery carriers, Liu, M.; Frechet, J. M., *J. Proc. Am. Chem. Soc. Polym. Mater. Sci. Engr.*, 80 at 167 (1999); Uhrich, K., *TRIP*, 5 at 388–393 (1997); Liu, H.; Uhrich, K. Proc, *Am. Chem. Soc. Div. Polym. Chem.*, 38 at 1226 (1997), chromatography stationary phases, Matthews, et al., *Prog. Polym. Sci.*, 23 at 1–56 (1998), boron neutron capture therapy agents, Newkome, et al., *Dendritic Macromolecules: Concepts, Syntheses, Perspectives*; VCH: Weinheim, Germany (1996); Newkome, G. R., *Advances in Dendritic Macromolecules*; JAI Press: Greenwich, Conn., Vol. 2 (1995), and magnetic resonance imaging contrast agents. Tomalia, D. A. *Adv. Mater.*, 6 at 529–539 (1994).

The dendriditic architecture of dendrimers provides a very high number of functional groups in a compact space. Because of this property, it is reasonable to expect that these novel molecules will play a major role in materials whose performance depends on high local concentration, such as drugs or antimicrobial agents.

The versatile chemistry of the dendrimers can also include metal atoms. The metal can be either an integral part of the dendrimer, such as in the building block, core, or terminal group, or it can associate with the dendrimer through interactions with branching units. These metals can be metal cations, metal salts, metal oxides or even elemental metal. Newkome and coworkers published a recent comprehensive review on dendrimers with metals (metallodendrimers) G. R. Newkome, E. He, C. N. Moorefield, *Chem. Rev.* 1999, 99, 1689. Metal salts, such as silver, are known antimicrobial agents. Dendrimer nanocomposites, formed by dendrimers and antimicrobial salts, offer a new way to deliver or enhance the antimicrobial properties of these agents.

Balogh et al. synthesized dendrimer nanocomposites, dendrimers with inorganic silver or silver ions, and tested their antibacterial properties. Balogh, L. *Proc. Am. Chem. Soc. Div. Colloi. & Surf. Chem.*, 54. (1999). For these dendrimer nanocomposites, the dendrimer itself does not have any antibacterial property. The activity comes from the silver/silver ions. In contrast, the quaternary ammonium functionalized dendrimers of the current invention derive antibacterial properties from the dendrimer itself. The dendrimers of the current invention are different from all previous investigations in that the surface groups of the dendrimers were transformed into quaternary ammonium groups. Unlike known QACs, the quaternary ammonium functionalized dendrimers of the current invention are more effective against Gram-negative bacteria such as *E. coli* and Gram-positive bacteria such as *S.aures*.

SUMMARY OF THE INVENTION

The inventors have successfully synthesized novel dendrimer biocides. These dendrimer biocides are fully described in U.S. patent application Ser. No. 09/588,585, which is herein incorporated by reference for all purposes. The present invention is directed to novel dendrimer biocide-silver complexes, which are new nanocomposites synthesized from the dendrimer biocides of the U.S. patent application Ser. No. 09/588,585 and silver salts. The hybrid structures embodying the present invention provide even more potent antimicrobial properties.

The structure investigated in this study is not very clear. A tentative name of "dendrimer-silver nanocomposite" was used. The potent biocide properties of the dendrimer-silver nanocomposites according to the invention all came by surprise to the inventors.

In the copending patent application Ser. No. 09/588,585, the described dendrimer biocides are capable of killing anthrax spores. However, the inventors have unexpectedly found that the dendrimer biocide-silver nanocomposites have superior biocide properties. The synergy between the dendrimer biocide and the silver ion has great potential for denaturing spores. Because spores are a significant class of biological weapons, the present invention would be useful in combating biological warfare weapons.

Traditional antibiological warfare agents are known to be very reactive and extremely toxic. Such agents include chlorine, formaldehyde, and peroxygen. In contrast, the novel dendrimer biocide-silver nanocomposites of the present invention are nonreactive and are virtually nontoxic to human skin. Similar compounds have been used in hand-wash formulations. Thus, the invention may provide an effective antibiological warfare agent. Examples of uses for the present invention include a denaturing spray or soldier uniforms impregnated with the invention.

Additionally, the invention can also be used in any situation that requires a potent biocide that is also environmentally stable. These applications include incorporation into protective coatings or paints, personal products such as cosmetics, industrial products, hospital products, and sanitation of swimming pools and spas. The invention can also be immobilized onto the surface to create efficient antimicrobial surfaces for use as biomaterials, antifouling paints, and other similar devices.

The object of the invention is to provide a dendrimer biocide-silver complex, and the method of using the dendrimer biocide-silver complex as an antimicrobial agent.

In accordance with the invention, silver nitrate ($AgNO_3$) is added to a dendrimer biocide solution to obtain a novel dendrimer-silver complex containing both dendrimer and silver ions.

DESCRIPTION OF FIGURES

FIG. 1. Plot showing the antibacterial activity of dendrimer-silver nanocomposites compared to dendrimer biocide alone.

DETAILED DESCRIPTION OF THE INVENTION

The novel dendrimer biocide-silver composite compositions of the present invention are prepared by reacting a dendrimer biocide with silver compound. The dendrimer biocides of the present invention are fully described in U.S. patent application Ser. No. 09/588,585, which is herein incorporated by reference. The dendrimer biocides of the present invention are the quaternary ammonium functionalized dendrimers of Formula I:

(I)

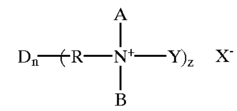

where D is a dendrimer; n is the generation number of the functionalized dendrimer; z is an integer less than or equal to 2(n+1); $X^-$ is an anion; R is a linking group; Y is an alkyl group or aryl group; A is an alkyl group or aryl group, and B is an alkyl group or aryl group. The quaternary ammonium functionalized dendrimers are then reacted with silver compound to form the dendrimer biocide-silver nanocomposites of the present invention.

To simplify the naming of the dendrimer biocides used in the present invention, a shorthand of "DnXNY" based on Formula 1 is used. In this shorthand format, D is a poly (propylene imine) ("PPI") dendrimer of generation n and having an anion X and a Y group. For example, "D3ClNC8" denotes a dimethyloctyl ($C_8$) ammonium (N) chloride (Cl) functionalized PPI generation 3 dendrimer (D3).

The dendrimer biocide-silver nanocomposites are prepared by a process comprising the following steps:

(1) adding excess $AgNO_3$ to the dendrimer biocide solution to convert the chloride ion of the dendrimer biocide to a nitrate ion;

(2) removing any precipitated AgCl;

(3) removing any remaining $AgNO_3$ in the solution by adding excess NaCl to the supernatant liquid; and (4) diafilter to remove remaining NaCl.

In a preferred embodiment greater than 1 percent stoichiometric amount of a silver compound may be used to prepare the dendrimer biocide-silver nanocomposite.

In the above process, the inventors unexpectedly found that there was still some silver ions left in the solution even when excess NaCl was added in step 3. These silver ions seemed to prefer to stay associated with the dendrimer rather than forming AgCl precipitate.

The inventors further discovered that the dendrimer biocide-silver nanocomposite structures are only stable in water. If the water was evaporated under vacuum, redissolution was impossible and a dark powder of $Ag_2O$ was observed with powdered dendrimer biocide residue. Because of these observations, the inventors believe that the novel dendrimer biocide-silver nanocomposite compounds contain both dendrimer and silver ions. While not wishing to be bound to a particular theory, the inventors believe that the silver ions may be absorbed on or complexed with the dendrimer. Depending on the composition of the solution, these nanocomposites can be stable for more than 3 months compared to several-hour stability of other dendrimer-nanocomposite preparations.

EXAMPLES

Preparation

Dendrimer biocide-silver nanocomposites were prepared by initially reacting silver nitrate ($AgNO_3$) with a D3ClNC8 dendrimer biocide to prepare a dendrimer biocide with nitrate counter-anion. The dendrimer biocide with nitrate counter-anion was prepared according to the method described above as follows:

1. Adding excess $AgNO_3$ to a D3ClNC8 solution to convert the chloride anion of the dendrimer to nitrate ion;

2. Precipitated AgCl was then centrifuged and excess NaCl solution was added to the supernatant liquid to remove any remaining $AgNO_3$ in the solution;
3. After a dialysis to remove the remaining NaCl, a dendrimer biocide with $NO_3$-counter-anion is obtained.

Preparation of Ag-200

The sample Ag-200 refers to the sample when a 200 percent stoichiometric amount of $AgNO_3$ was used in preparing the dendrimer biocide-silver nanocomposite. Approximately 0.1 gram of D3ClNC16 is dissolved in minimal amount of ethanol and dilute with water to obtain 10 mL solution. 10 mL of 0.1N AgNO3 is then added to change the counter anion of the dendrimer to nitrate. The solution is then centrifuged at 3000 g for 2 hours. The supernatant is collected and 10 mL of 0.1N NaCl is added to remove the residual amount of AgNO3 in the solution. The excess NaCl was then removed with diafiltration of distilled water (1000 MWCO membrane). The final volume after diafiltration can be adjusted according to the desired concentration. Typically a 100 mL solution is achieved.

Preparation of Ag-500

The sample Ag-500 refers to the sample when a 500 percent stoichiometric amount of $AgNO_3$ was used in preparing the dendrimer biocide-silver nanocomposite. Approximately 0.1 gram of D3ClNC16 is dissolved in minimal amount of ethanol and dilute with water to obtain 10 mL solution. 25 mL of 0.1N AgNO3 is then added to change the counter anion of the dendrimer to nitrate. The solution is then centrifuged at 3000 g for 2 hours. The supernatant is collected and 25 mL of 0.1N NaCl is added to remove the residual amount of AgNO3 in the solution. The excess NaCl was then removed with diafiltration of distilled water (1000 MWCO membrane). The final volume after diafiltration can be adjusted according to the desired concentration. Typically a 100 mL solution is achieved.

Measurement of Antimicrobial Properties

The antimicrobial properties of these composites were evaluated using a bioluminescence method. For these bioluminescence experiments, several strains of recombinant *E. coli* are used. The recombinant *E. coli* strains containing a fusion of *Escherichia coli* heat shock promoters and a lux gene of *Vibrio fischeri* were developed at DuPont. Relevant information regarding various strains is known to those skilled in the art.

*E. coli* stock solutions, kept at −80° C. freezer until required for use, were prepared in Lucia-Barton (LB) media supplemented with 20% glycerol. Glycerol was added to protect bacteria during freezing and thawing processes. During inoculation, a required amount of *E. coil* suspension (typically 10%) was added to fresh and sterile LB broth and incubated overnight at 37° C. These cells were also centrifuged and washed twice with phosphate buffered saline. Cell concentration was determined using a Petroff-Hausser counting chamber (Scientific Products, Edison, N.J.). Bacteria suspensions were then diluted to the test concentration. The recombinant *E. coli* strains were also stocked in a similar way to the wild-type *E. coli*. The medium used was Lucia-Barton (LB) supplemented with 25 mg/ml kanamycin monosulfate to maintain the plasmid. These plasmid-containing strains were grown to an early exponential phase at 30° C. The temperature used was lower than normal because enzymes responsible for generating light would be deactivated at 37° C. These cells were also centrifuged and washed twice with 0.1% peptone water before use.

There are a variety of methods that can be used to evaluate the antimicrobial properties of new materials. Method selection often depends on specific applications. Antimicrobial test results might be reported qualitatively, using terms as sensitive, intermediate, or resistant, or quantitatively in terms of concentration of an agent needed to inhibit or kill bacteria. Suspension tests are typically used to evaluate water-soluble antimicrobials, while surface antimicrobial tests are designed to characterize the antimicrobial properties of non-leaching biocidal materials.

During suspension tests, the effectiveness of biocides was quantified by mixing a suspension of viable bacteria and a certain concentration of test materials and monitoring the subsequent number of live cells at distinct time points. Bacteria were grown overnight and harvested as described. The plate-count method and bioluminescence test methods are two ways to quantify live cells.

In using the plate-count method, cells were re-suspended in a PBS buffer at a concentration between $1 \times 10^8$ and $1 \times 10^9$ cells/ml in sterile, 15-ml polypropylene centrifuge tubes (VWR Scientific Products, West Chester, Pa.). The viable cell concentration was determined by making a series of 10-fold dilutions of the cell suspension and spreading the bacteria on agar plates. The plates were then incubated over night at 30° C. for recombinant *E. coli* and 37° C. for wild-type *E. coli*. The visible colonies on the plates were then counted in 24–48 hours. Each colony represents one viable bacterium from the original suspension. The number of colonies, multiplied by the dilution, provides a measure of the viable cells in the original suspension.

In these studies, a dendrimer biocide was added to a cell suspension. The suspension was then agitated thoroughly with a vortexer (Scientific Products, McGraw Park, Ill.). Aliquots of the suspension were removed after 15, 30, and 60 minutes of biocide exposure. The aliquots were immediately used in a series of 10-fold dilutions with buffer containing 10% Tween 80 (Aldrich Chemical Company, Milwaukee, Wis.), which was utilized as a deactivating agent for the quaternized moieties. Without the denaturing agents, test samples would continue to exert its toxic influence, thereby increasing the apparent activity of the biocide.

For the bioluminescence experiments, several strains of recombinant *E. coli* were used. These recombinant *E. coli* strains containing a fusion of *Escherichia coli* heat shock promoters. Whenever bacteria receive stress from a toxic compound, the intensity of light emitted from the bacteria will change. From a "light-on" or "light-off" response one can obtain real-time cell viability data. Strain TV 1048, in which the lux operon is coupled to the promoter of lac operon, was used in this study. Bioluminescence is observed under normal growth conditions. Whenever the bacteria are in a biocidal environment, the light-off response quantitatively corresponds to the antibacterial effect.

During experiments, these plasmid-containing strains were grown to an early exponential phase at 30° C. in LB medium and then incubated with a known amount of the test sample. Bioluminescence was measured either in real time or at some time intervals using a luminometer (Model 20e, Turner Design, Calif.) and the data were recorded by a computer with data collection capacity.

The antibacterial property of the D3ClNC8 dendrimer biocide-silver nanocomposite against Gram-negative *E. coli* was determined by a bioluminescence method. Bioluminescence is observed under normal growth conditions for the recombinant *E. coli* strain TV 1048. Whenever the bacteria are in a biocidal environment, the light-off response corresponds to the toxic effect of the biocide. The result is expressed as the sample bioluminescence normalized to a control (without biocidal dendrimer of the present invention) versus time. The reduction of luminescence quantitatively shows the antibacterial activity of the sample. At 4 ppm, the dendrimer biocide inhibited the growth of *E. coli*, but the bacteria could adjust to the environmental stress and survive. At higher concentrations (20 ppm), the bioluminescence decreased very rapidly and went down to undetectable levels in 15 min indicating a strong biocidal effect. In a control experiment, the bioluminescence of the bacteria did not change much (5%) if the same concentration of pure PPI generation 3 dendrimers was added.

The sample Ag-200 refers to the sample when a 200 percent stoichiometric amount of $AgNO_3$ was used in preparing the dendrimer biocide-silver nanocomposite. The Ag-200 formulation was observed to be much more potent than the dendrimer biocide alone. See FIG. 1. This figure shows that 2 ppm of D3ClNC8 reduces the bioluminescence to only 10 percent of the bioluminescence of the control. However, formulation Ag-500, containing only 0.8 ppm of D3ClNC8 and less than 0.8 ppm of $Ag^+$ can reduce the bioluminescence to 0.1 percent of the control. The exact silver concentration was unknown since some AgCl precipitate consumed $Ag^+$). The more potent formulation, Ag-200 with 0.8 ppm of D3ClNC8 and less than 0.3 ppm of $Ag^+$ can reduce the bioluminescence to 0.001 percent of the control, which corresponded to a 5-order of magnitude reduction. The inventors further observed that the Ag-200 formulation is unexpectedly more potent than Ag-500 formulation.

The improvement of the potency may be explained by synergy between the dendrimer biocide and silver ions. Silver ions have been used as antimicrobials for 4000 years. The mode of action of silver ion is similar to $Hg^{2+}$. Both ions can complex with electron donor groups containing sulfur, oxygen or nitrogen. Silver parallels mercuric ions in relative affinities for various proteins, but is somewhat less tightly bound. Synergism is defined as the ability of two antimicrobials acting together to markedly increase the rate of the bacteriocidal action as compared to the rate of each antimicrobial alone. A typical example of synergy is between EDTA and QACs. EDTA is able to chelate the calcium and magnesium, thus destabilizes the phospholipid membrane and promotes the membrane-disrupting action of QACs.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. A dendrimer biocide-silver nanocomposite composition comprising a quaternary ammonium dendrimer biocide of Formula I:

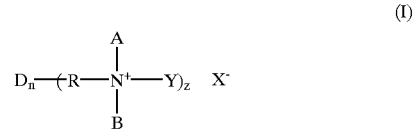

where:

D is a dendrimer;

n is the generation number of the functionalized dendrimer;

z is an integer less than or equal to 2(n+1);

X is an anion;

R is a linking group;

Y is an alkyl group or aryl group;

A is an alkyl group or aryl group, and

B is an alkyl group or aryl group and silver ions associated with said dendrimer biocide, wherein a 200 percent stoichiometric amount of a silver compound is used to prepare the dendrimer biocide-silver nanocomposite.

* * * * *